(12) United States Patent
Korst et al.

(10) Patent No.: US 12,417,848 B2
(45) Date of Patent: Sep. 16, 2025

(54) PREDICTION TOOL FOR PATIENT IMMUNE RESPONSE TO A THERAPY

(71) Applicant: KONINKLIJKE PHILIPS N.V., Eindhoven (NL)

(72) Inventors: Johannes Henricus Maria Korst, Eindhoven (NL); Reinhold Wimberger-Friedl, Waalre (NL); Vanda Lucia De Carvalho Vittorino de Almeida, Veldhoven (NL); Koen De Laat, Udenhout (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 294 days.

(21) Appl. No.: 17/762,753

(22) PCT Filed: Sep. 18, 2020

(86) PCT No.: PCT/EP2020/076074
§ 371 (c)(1),
(2) Date: Mar. 23, 2022

(87) PCT Pub. No.: WO2021/058385
PCT Pub. Date: Apr. 1, 2021

(65) Prior Publication Data
US 2022/0367062 A1      Nov. 17, 2022

(30) Foreign Application Priority Data
Sep. 25, 2019   (EP) .................................... 19199689

(51) Int. Cl.
G16H 50/30   (2018.01)
(52) U.S. Cl.
CPC .................................. *G16H 50/30* (2018.01)

(58) Field of Classification Search
CPC ........ G16H 50/30; G16H 50/20; G16H 70/40; G16H 20/00; G16H 10/60
See application file for complete search history.

(56) References Cited

U.S. PATENT DOCUMENTS

| 2014/0172398 A1 | 6/2014 | Hoeng et al. |
| 2015/0262559 A1 | 9/2015 | Beck |

(Continued)

FOREIGN PATENT DOCUMENTS

| CN | 108624650 A | 10/2018 |
| WO | 2016168133 A1 | 10/2016 |
| WO | 2019008364 A1 | 1/2019 |
| WO | 2019108135 A1 | 6/2019 |

OTHER PUBLICATIONS

Blank et al "The Cancer Immunogram" Science vol. 352 2016 p. 658-660.

(Continued)

*Primary Examiner* — Meredith A Long

(57) ABSTRACT

Aspects and embodiments relate to a method and apparatus configured to perform that method. The method relates to generating an indication of relevance associated with a selected biological phenomenon indicative of condition of an immune system of a patient, that selected biological phenomenon being associated with response of a patient to a chosen therapy. The method comprises steps of: determining one or more measurable input parameters characteristic of the patient and associated with the biological phenomenon; mapping the one or more input parameters to a contribution to a score associated with the selected biological phenomenon; and combining the mapped contributions across the one or more input parameters to calculate the score associated with the selected biological phenomenon. A decision support system in accordance with aspects and embodiments may be configured to provide a score and/or visualisation, for example, a numerical value or graphical (Continued)

representation, relating to one or more underlying biological phenomena contributing to immune response or immune condition of a patient to a therapy. The underlying biological phenomena may be quantified using various biomarkers and/or measurable input parameters.

20 Claims, 5 Drawing Sheets

(56) References Cited

U.S. PATENT DOCUMENTS

| | | | | |
|---|---|---|---|---|
| 2015/0363559 | A1* | 12/2015 | Jackson | G16B 20/20 |
| | | | | 705/2 |
| 2018/0258125 | A1 | 9/2018 | Mao et al. | |
| 2018/0322955 | A1* | 11/2018 | Sevenster | G16H 50/30 |
| 2018/0358125 | A1* | 12/2018 | Bagaev | G16B 40/30 |
| 2019/0138846 | A1* | 5/2019 | Durrleman | G06F 18/295 |

OTHER PUBLICATIONS

Van Dijk et al "The Cancer Immunogram as a Framework for Personalized Immunotheraphy in Urothelial Cancer" European Urology, 2018.
Cona et al "Combination of Baseline LDH, Performance Status and Age as Integrated Algorithm to Identify Solid Tumor Patients . . . " Cancers, 2019 vol. 11.
Lin et al "Correct and Logical Inference on Efficacy in Subgroups and Their Mixture for Binary Outcomes" Biometrical Journal Sep. 18, 2018.
Nosrati et al "Evaluation of Clinicopathological Factors in PD-1 Response: Derivation and Validation . . . " British Journal of Cancer 2017 vol. 116, p. 1141-1147.
International Search Report and Written Opinion from PCT/EP2020/076074 mailed Dec. 10, 2020.
Wiegink "Atezolizumab as First Line Treatment for Selected Patients with Advanced or Metastatic Carcinoma" Master Thesis Jun. 2, 2018.

* cited by examiner

PREDICTION TOOL FOR PATIENT IMMUNE RESPONSE TO A THERAPY

CROSS REFERENCE TO RELATED APPLICATIONS

This application is a U.S. national phase application of International Application No. PCT/EP2020/076074 filed Sep. 18, 2020, which claims the benefit of EP Application Serial No. 19199689.1 filed Sep. 25, 2019 and is incorporated herein by reference.

FIELD OF THE INVENTION

The invention relates to the field of therapeutics and more particularly to an assessment of likely relevance of a biological parameter to response of a patient to a particular therapy.

BACKGROUND OF THE INVENTION

Various therapeutic options may be available to a clinician when determining a course of action in relation to a patient. Therapies in relation to cancer treatment may, for example, include: immunotherapy, radiotherapy and chemotherapy. Those therapies may be applied to a patient as a monotherapy or in combination.

Immunotherapies represent one possible path available to a clinician in relation to treatment of various patient conditions. Immunotherapies, radiotherapies and chemotherapies may be expensive and may be such that whilst they can offer a substantial clinical benefit to some patients, other patients may not benefit. Occasionally, use of a monotherapy or combination of therapies in relation to patient treatment can result in serious adverse events.

As a result, consideration of whether a given patient may benefit from a given therapy, based on a broad range of biomarkers indicated by, for example, medical imaging scans, histo- and molecular pathology, and/or blood-based measurements, has been recognised as being beneficial.

Understanding and managing a growing body of knowledge regarding an indication of immune status of a patient; interpretation of combinations of biomarkers in an immune context and implications of variants represents an ongoing challenge to clinicians.

By way of example: in relation to cancer treatment checkpoint immunotherapies are one cancer treatment methodology. For several types of cancer they may be considered as first-line treatment. Typically comprehensive knowledge of immune oncology, immunotherapeutics and their contraindications, within specific molecular and clinical contexts, will be required to assess suitability of a patient and immunotherapy combination. Such knowledge is considered in the context of a patient's specific disease, histology, radiology, and clinical data, for example, prior treatment, stage and progression of disease. A vast range of variables may need to be factored in when deciding upon a treatment strategy for a patient. It is generally difficult for clinicians to decide whether or not to select immunotherapy for a given cancer patient.

The present invention recognises that it may be helpful to offer a clinician a structured mechanism to assess information available in relation to each patient and a possible applicable therapy.

SUMMARY OF THE INVENTION

A first aspect of the invention relates to a method of generating an indication of relevance associated with a selected biological phenomenon indicative of condition of an immune system of a patient, the selected biological phenomena being associated with response of a patient to a chosen therapy, the method comprising: determining one or more measurable input parameters characteristic of the patient and associated with the biological phenomenon; mapping the one or more input parameters to a contribution to a score associated with the selected biological phenomenon; and combining the mapped contributions across the one or more input parameters to calculate the score associated with the selected biological phenomenon.

According to some embodiments, calculating the score associated with the selected biological phenomenon comprises: determining an absence of available measurable input parameters of relevance to one or more the selected biological phenomenon and setting a neutral contribution to the selected biological phenomenon for which there is an absence of available measurable input parameters; and combining the mapped contributions across the one or more input parameters to calculate the score associated with the selected biological phenomenon.

According to some embodiments, the one or more measurable input parameter of the patient comprises a plurality of interchangeable measurable input parameters, having different reliability rankings, and the method comprises: selecting one or more of the interchangeable measurable input parameters having higher reliability ranking than the remaining measurable input parameters.

According to some embodiments, the method comprises determining a confidence interval for the score associated with the biological phenomena, the determination comprising a function of the one or more measurable input parameters characteristic of the patient.

According to some embodiments, determining a confidence interval for the score associated with the biological phenomenon comprises: determining a confidence interval and indication of reliability associated with the one or more measurable input parameters mapped to a selected biological phenomenon; and generating a confidence interval associated with the biological phenomenon based on the mapped contributions across the one or more input parameters.

According to some embodiments, when the biological phenomenon comprises inflammatory status, the one or more measurable input parameters comprise one or more of: IL-6, CRP and albumin concentration, neutrophil and lymphocyte count, body mass index and similar analogous measurable parameters.

According to some embodiments, when the biological phenomenon comprises checkpoint expression, the one or more measurable input parameters comprise one or more of: PD-L1 or CTLA-4 and similar analogous measurable parameters.

According to some embodiments, when the biological phenomenon comprises tumour foreignness, the one or more measurable input parameters comprise one or more of: TMB; MSI or Smoking status and similar analogous measurable parameters.

According to some embodiments, when the biological phenomenon comprises immune infiltrate, the one or more measurable input parameters comprise one or more of: NAB (neo-antigen burden); TIL; CD8, CD3, CD4, macrophages, MDSC and similar analogous measurable parameters.

According to some embodiments, when the biological phenomenon comprises tumour metabolism, the one or more measurable input parameters comprise one or more of: LDH, SUV and TLG and similar analogous measurable parameters.

According to some embodiments, when the biological phenomenon comprises T cell dysfunction, the one or more measurable input parameters comprise one or more of: PD-1; LAG-3; TIM-3 and similar analogous measurable parameters.

According to some embodiments, the method further comprises combining the one or more indication of relevance of one or more biological phenomena to response of the patient to generate an indication of overall response of the patient to the chosen therapy.

According to some embodiments, combining the one or more indication of relevance comprises: selecting a plurality of biological phenomena of relevance to suitability of a patient for the chosen therapy, the biological phenomena comprising one or more phenomenon indicative of condition of an immune system of the patient; determining the calculated score associated with each of the selected biological phenomena; assigning a significance to the selected biological phenomena to an overall response of the patient to the chosen therapy; and combining the calculated score and assigned significance across the selected plurality of biological phenomena to generate the indication of overall response of the patient to the chosen therapy.

According to some embodiments, the method comprises: generating a quantitative indication of relevance of each the selected plurality of biological phenomena to the overall response of the patient to chosen therapy.

According to some embodiments, assigning a significance to the selected biological phenomena comprises weighting the phenomena according to whether they have a positive or negative impact upon response of the patient to the chosen therapy.

According to some embodiments, combining the one or more indication of relevance of one or more biological phenomena to the overall response of the patient to generate the indication of overall response of the patient to the chosen therapy comprises one or more of: linear combination of the calculated score and assigned significance; quadratic or higher order combination of the calculated scores and assigned significance, a Bayesian network combination of scores and assigned significance.

According to some embodiments, the method comprises: generating a confidence interval for the indication of overall response of the patient to the chosen therapy using a determined confidence interval for each score associated with the selected plurality of biological phenomena and the combination selected for combining the calculated score and assigned significance across the selected plurality of biological phenomena.

According to some embodiments, the chosen therapy comprises: checkpoint inhibition immunotherapy for treatment of cancer.

According to some embodiments, the chosen therapy comprises: checkpoint inhibition immunotherapy for treatment of cancer used as a monotherapy.

According to some embodiments, the chosen therapy comprises: immunotherapy for treatment of cancer for use in combination with one or more other therapies.

According to some embodiments, the chosen therapy comprises: checkpoint inhibition immunotherapy for treatment of cancer for use in combination with one or more other cancer therapies.

According to some embodiments, the chosen therapy comprises: checkpoint inhibition immunotherapy for treatment of cancer in combination with radiotherapy or chemotherapy.

According to some embodiments, the biological phenomena of relevance to suitability of a patient for the chosen therapy comprise: clinically understandable biological phenomena relevant to expected response of the patient to the chosen therapy.

According to some embodiments, the therapy comprises a cancer treatment therapy and the biological phenomena comprise one or more of: tumour foreignness; tumour metabolism; tumour aggressiveness; inflammatory status; tumour infiltration, T-cell dysfunction; checkpoint expression.

According to some embodiments, the therapy comprises a cancer treatment therapy and the biological phenomena comprise at least three of: tumour foreignness; tumour metabolism; tumour aggressiveness; inflammatory status; tumour infiltration, T-cell dysfunction; checkpoint expression.

A second aspect of the invention relates to computer program product operable, when executed on a computer, to perform the method of the first aspect.

A third aspect of the invention relates to an apparatus configured to generate an indication of relevance associated with a selected biological phenomenon indicative of condition of an immune system of a patient, the selected biological phenomena being associated with response of a patient to a chosen therapy, the apparatus comprising: memory having computer readable instructions stored therein; and a processor configured to execute the computer readable instructions to: determine one or more measurable input parameters characteristic of the patient and associated with the biological phenomenon; map the one or more input parameters to a contribution to a score associated with the selected biological phenomenon; and combine the mapped contributions across the one or more input parameters to calculate the score associated with the selected biological phenomenon.

According to some embodiments, the apparatus may comprise a user interface configured to communicate said score associated with the selected biological phenomenon to a user.

Further particular and preferred aspects are set out in the accompanying independent and dependent claims. Features of the dependent claims may be combined with features of the independent claims as appropriate, and in combinations other than those explicitly set out in the claims.

Technical advantages of the invention and various possible implementations of the invention are set out in more detail in relation to the description of embodiments of the invention.

Advantages of the invention may include provision of support for clinical decision making concerning selection of a patient for therapy, or a therapy for a patient, for example, an immune therapy comprising a checkpoint inhibition immunotherapy.

Advantages of the invention may include allowing a clinician to understand and visualise a contribution being made by one or more particular clinically understandable biological states to the immune condition of a patient.

Advantages of the invention may include facilitation of generation of a quantitative measure of an overall likely response of a patient to a selected therapy.

Advantages of the invention may include providing an estimate of success of a selected therapy based on an analysis of multimodality input data of relevance to a patient, as well as providing a confidence interval for such an estimate so as to quantify its reliability.

Advantages of the invention may include providing a patient condition overview from an automated system processing multimodality input data of relevance to a patient.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which:

FIG. 5b illustrates a transfer function for use with an input parameter of the example of FIG. 5a.

DESCRIPTION OF EMBODIMENTS OF THE INVENTION

Figure 1A:
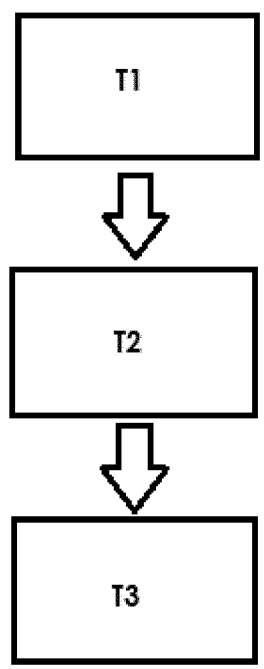
FIG. 1a illustrates schematically a method according to one arrangement.

Before describing specific illustrative examples in detail, a general overview is provided.

Arrangements may provide a model that provides an indication of relevance of one ore more biological phenomena to response of a patient to a possible therapy, for example, one or more cancer therapy. That possible cancer therapy may include, for example, an immunotherapy. Arrangements may comprise a method with an output suitable to support a clinical decision making process. Given high costs associated with therapies, restricted patient response and potential adverse events, it is important to select patients who are likely to respond positively to a therapy. A model in accordance with the invention is configured to accept a large number of clinical and diagnostic parameters from various diagnostic modalities. Such modalities can include, for example, radiology, pathology and clinical chemistry. Arrangements may allow for translation of the parameters into a quantitative numerical biological "result" or set of results. Some arrangements allow for those results or score to be combined into an explicit estimate of a response probability, or a score, in relation to an individual patient. Each numerical result, including the estimate of response probability, may include an indication of a corresponding confidence interval.

The complexity of any score associated with a biological parameter of potential significance to immune response of a patient is increased since some input parameters have a positive influence on a response of a patient and some have a negative influence. Some input parameters are of more significance and others of less significance to a score. Often one or more input parameters can be generally correlated. As a result, without some quantitative analysis method, it becomes difficult to form a clear view of a score to be associated with a biological parameter of potential significance in relation to a candidate therapy or therapies to be assigned given patient.

Furthermore, when creating a view of an overall picture of immune condition of a patient, some biomarkers are of more significance and others of less significance to likely response. Often one or more biomarkers can be generally correlated. As a result, without some quantitative analysis method in relation to individual biomarkers and combinations of available biomarkers, it becomes difficult to form a clear view of a likely response of a given patient to a selected therapy.

Arrangements may have an ability to appropriately account for missing data in a manner which is transparent to a user. Missing data may typically influence both response estimate and corresponding confidence interval. Arrangements may allow for any impact of missing data, or steps taken to mitigate or account for missing data, to be commensurate with likely significance of such missing data.

Arrangements recognise that even if complete information is available, it can be difficult for a clinician or user to estimate a score relating to an individual biomarker or biological parameter determined to be of relevance to immune condition of a patient, and/or to provide a repeatable objective score providing a view of overall response, taking into account more than one biological parameter, of a patient to a particular therapy. That estimate is even more difficult when some biomarkers are unavailable at a decision point.

One known mechanism for patient assessment comprises a cancer immunogram proposed by Blank, Haanen, Ribas & Schumacher [SCIENCE 2016 May 6 352(6286):658-60: CANCER WIMUNOLOGY: The "cancer immunogram"]. Such an immunogram visualizes seven different dimensions with multiparameter biomarkers each. The state of a patient can be visualized by a spider web. The various features that may be included are diverse. In practice often not all features included are available.

A visual indication such as that provided by an immunogram does not give an explicit estimate of the response probability, nor does it provide a clear indication of whether the effect of specific quantities of each of the included biomarkers is positive or negative. Even in the case where biomarker quantities are set such that the larger their quantity the higher the response probability, an overall estimate of a response probability associated with a patient may not be easily derived by clinicians. Whilst total area enclosed by the selected biomarkers may provide some quantitative assessment, that area depends on cyclic ordering of the chosen biomarker features. In other words, contribution to the total area as an estimate of the response probability for a patient which is associated with a given biomarker depends upon the quantities of neighbouring biomarkers included in the immunogram. Hence, in addition to the biological correlation between biomarkers, use of a total enclosed area of an immunogram creates an additional dependency between biomarkers and serves to complicate appropriate interpretation of input quantities.

It will also be appreciated that an immunogram may not appropriately account for missing data of relevance to an estimate of response probability. If one or more quantity is an unknown, then it is unclear how this can be accounted for within an immunogram. It will be appreciated that simply setting a missing value to zero, or to average may result in creation of an immunogram in which enclosed area provides an overview which may be distorted.

Alternative approaches use machine-learning techniques to estimate response probability based on a set of measurements from multiple patients. Examples of machine learning algorithms include random forests, support vector machines and/or (deep) neural networks. The machine-learning techniques operate as a black box and produce results that may not easily be interpreted by clinicians. Machine learning techniques typically do not produce results which transparently use and/or quantify biological phenomena which would be interpretable by clinicians. Such approaches may therefore not be suited to inclusion in a decision support system that is intended to support the decision making of clinicians, since they produce a final estimate of the response probability without giving intermediate results interpretable by a clinician.

Arrangements described recognise that a computational model which is configured to estimate a score or scores, including, for example, patient response probability to a selected therapy based on all available data, would be very helpful. Such a computational model may be configured to combine and adapt to knowledge which is becoming available through research, experience, and publications in medical literature. Arrangements may provide a decision support system, in the form of a method or apparatus configured to perform that method.

A decision support system in accordance with described arrangements may be configured to provide a score and/or visualisation, for example, a numerical value or graphical representation, relating to one or more underlying biological phenomena contributing to immune response or immune condition of a patient to a therapy. The underlying biological phenomena may be quantified using various biomarkers and/or measurable input parameters. The result, probability or score generated by described arrangements may be such that they visualize or quantify phenomena which are interpretable by clinicians. In other words, the biological phenomena and the scores generated in relation to the biological phenomena, based on input parameters, represent concepts that clinicians are used to, to describe the condition of a patient.

The decision support system may include a computational model configured to estimate a response of a patient to a chosen therapy in relation to an individual patient or set of patients. The estimate of response of a patient may be based on a score associated with one or more biomarkers or biological phenomena. Those biomarkers may themselves be based on measurements from one or more different modalities including, for example, radiology (PET/CT), histopathology, and molecular biomarkers extracted from tissue and clinical chemistry (blood).

A decision support system in accordance with described arrangements may be configured to visualise an estimate or score indicative of likely response, for example, a response probability, for an individual patient or group of patients. The system may be configured to provide an indication of a confidence interval associated with the calculated estimate.

A decision support system in accordance with described arrangements may be configured such that it appropriately and intelligently may take into account missing data. That process may occur in relation to visualization and/or in relation to computation of estimates and scores and/or in relation to computation of a confidence interval.

A decision support system in accordance with described arrangements may be configured such that it provides an indication to a user of both quantity/influence of each biomarker and whether the influence of that biomarker on total response probability is positive or negative.

General Architecture

Arrangements provide a model, in the form of a method and apparatus configured to perform the method, which supports clinical decision making concerning the selection of a patient for a therapy, for example, immunotherapy. One particular application of arrangements concerns the assessment of patient suitability for checkpoint inhibition immunotherapy.

FIG. 1a illustrates schematically a method of generating an indication of relevance associated with a selected biological phenomenon indicative of an immune system condition of a patient. The selected biological phenomenon itself being associated with likely response of a patient to a chosen therapy. The method comprises steps as follows:

T1: determining one or more measurable input parameters characteristic of said patient and associated with said selected biological phenomenon;

T2: mapping said one or more input parameters to a contribution to a score associated with said selected biological phenomenon; and T3: combining said mapped contributions across said one or more input parameters to calculate said score associated with said selected biological phenomenon.

Figure 1B:
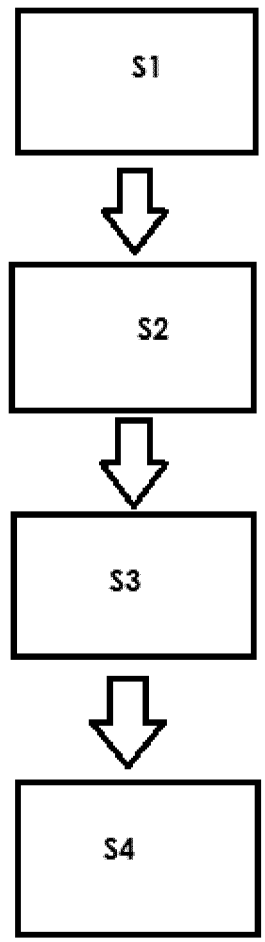
FIG. 1b illustrates schematically a method according to one arrangement.

FIG. 1b illustrates schematically a method which builds upon the method described in relation to FIG. 1a. FIG. 1b illustrates an arrangement in which steps of FIG. 1a can be used in a method of generating a quantitative indication of response of a patient to an immunotherapy. That method comprises steps as follows:

S1: selection of a plurality of biological phenomena of relevance to suitability of a patient for a therapy, in this case, immunotherapy, those biological phenomena comprising one or more phenomenon indicative of the condition of an immune system of the patient;

S2: calculation of a score associated with each of the selected biological phenomena;

S3: assignment of a significance to the selected biological phenomena to a response of said patient to the immunotherapy;

S4: combining the calculated score and assigned significance across the selected plurality of biological phenomena to generate the quantitative indication of response of the patient to the chosen immunotherapy.

The model may comprise several characteristics. It may use multimodality input data for several decision elements including: addressing eligibility; interfering medications or comorbidities; patient fitness; and significantly, models may include an assessment of probability that a patient is likely to respond to a particular immunotherapy. Input data may be sourced from patient medical records, patient clinical chemistry, histopathology, molecular pathology, radiology and similar.

The quantitative indication of overall response of a patient may comprise a response probability (RP). That response probability may comprise a continuous value from 0 to 1 and can be relative to a reference population or absolute as the probability that an objective response can be expected.

An overall score, for example, response probability, can be calculated according to a two-step method that can be characterized as: in a first step (S1 in FIG. 1b, described in more detail in relation to FIG. 1a) calculating a score or value relating to so-called biological phenomena or biological states (BS) that are relevant to the expected response of a patient. Examples of biological states or biological phenomena in relation to treatment and therapy relating to cancer include: tumour foreignness; tumour metabolism/aggressiveness; inflammatory status; tumour infiltration;

Tcell dysfunction; checkpoint expression. In a second step the BSs are combined (S4 in FIG. 1b) each with a particular weight (S3 in FIG. 1b) and normalized to a combined score of RP.

Figure 2:
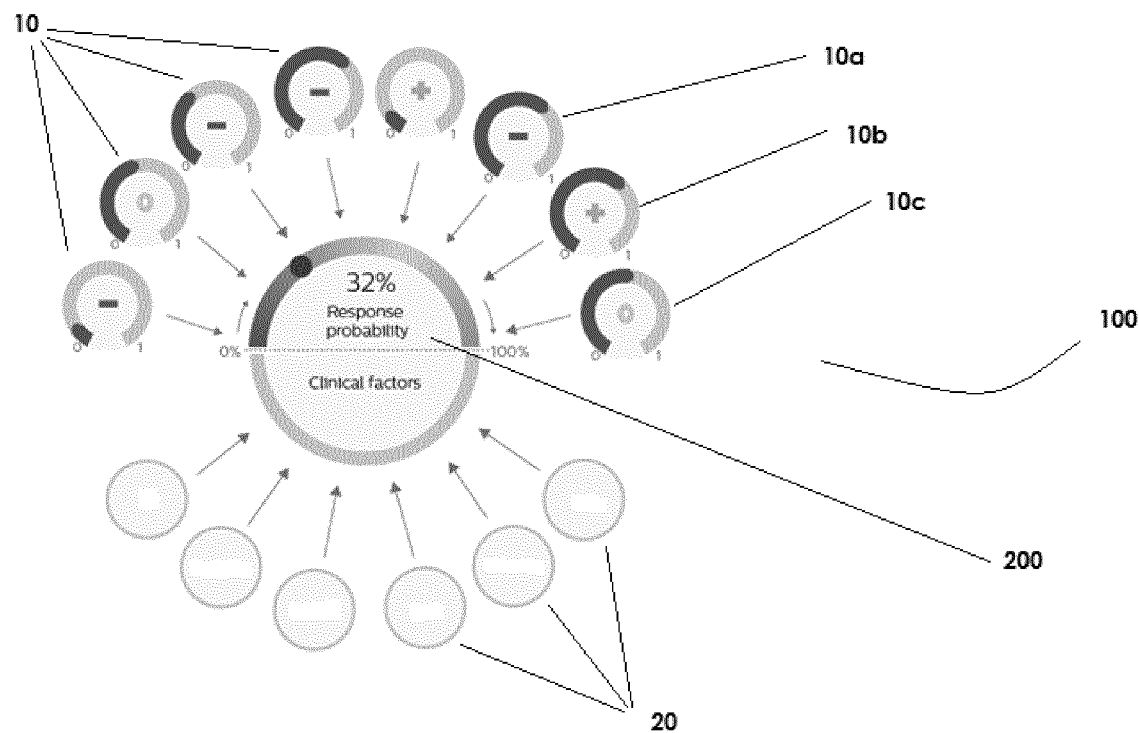
FIG. 2 illustrates schematically one possible arrangement for communication of output of a method such as that described in relation to FIG. 1a or 1b to a clinician.

FIG. 2 illustrates schematically one possible arrangement for communication of output of a method such as that described in relation to FIGS. 1a and 1b to a clinician. The output of a method or apparatus according to arrangements may comprise a visual dashboard type display 100. In the example shown in FIG. 2, eight biological phenomena 10 which may contribute to overall response of a patient have been selected and combined to form an estimate of patient response probability 200. The display 100 may also include clinical information of relevance to a patient 20, which may help a clinician to make a decision regarding the appropriateness of a given therapy to a patient.

In the example of FIG. 2, the biological phenomena 10 comprise: PD-L1 expression; Tumour Infiltrate; Tcell exhaustion; Eosinophils; Inflammatory Status; Tumour aggressiveness, Tumour foreignness and Tumour heterogeneity. Clinical information of relevance may include an indication of any comorbidities, whether the patient is taking steroidal medication, whether the patient is a smoker and similar. It will be understood that in some arrangements, clinical information 20 may not be directly used in creation of response probability 200.

In relation to FIG. 2, a calculated contribution or score of each biological phenomenon (see FIG. 1a) to an overall score 200 relating to likely patient response to a therapy or therapies 200. For example, biological phenomenon 10a has been calculated to be relatively high in terms of probability of presence in the patient under study (indicated by the relatively large part of the circle fraction between 0 and 1 which is shaded) and the presence of that biological phenomenon has a detrimental (negative) effect (indicated by the minus sign drawn inside the circle portion) upon the likelihood that a patient will respond positively to the immunotherapy under consideration. Biological phenomenon 10b is similarly likely to be present in the patient under study and that phenomenon is a positive indicator that the immunotherapy will be well received (indicated by the plus sign drawn inside the circle fragment) by a patient. Biological phenomenon 10c is neutral in terms of overall impact upon overall response probability of a patient to the immunotherapy. It may be that no information of relevance to that biological phenomenon is available to feed into the model.

Figure 3:
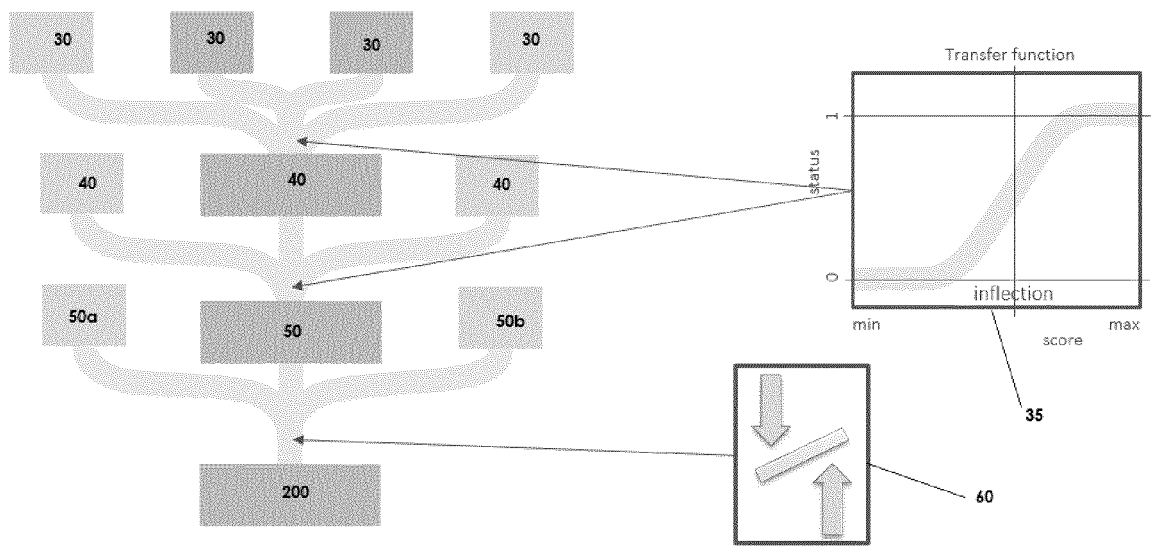
FIG. 3 illustrates schematically combining input parameters to form a biological parameter score relating to a patient.

Each biological phenomenon 10 score, for example, probability, can be calculated from a combination of related input parameters, which in many cases are of multimodal nature as described generally in relation to FIG. 1b. FIG. 3 illustrates schematically combining input parameters 30 to form a biological parameter score 50 associated with a patient. Each input parameter 30 may contributes according to a predefined transfer function. This is typically a sigmoidal curve with output from 0 to 1, with a predefined input range, inflection point and steepness as shown for example as graph 35. Several of these contributions 40 are combined and normalized to arrive at a score 50 in relation to a selected biological phenomenon. Estimates 50, 50a, 50b for different Biological Phenomena can, in some arrangements, each be given an appropriate weight 60 and combined to create an estimate of overall response probability 200.

Figure 4:
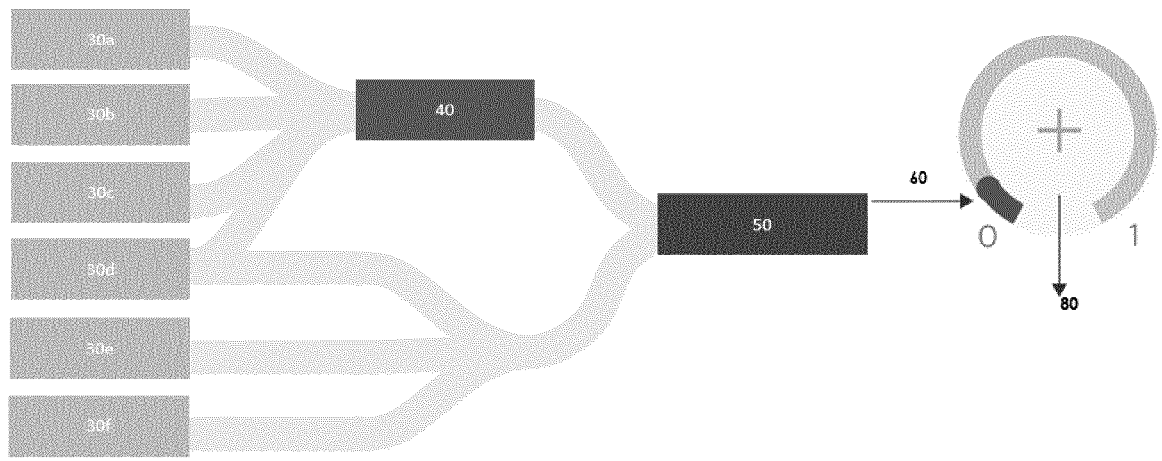
FIG. 4 illustrates one example of input parameters being combined to formulate a score associated with a selected biological phenomenon.

FIG. 4 illustrates one example of input parameters being combined to formulate a probability associated with a selected biological phenomenon. That process is described more generally in relation to FIG. 1a. As an example, input parameters for the biological phenomenon "inflammatory status" are shown in FIG. 4 and comprise: IL-6 30f, CRP 30e, and albumin concentration 30d, neutrophil count 30b and lymphocyte count 30c, body mass index 30a. One or more of the available inputs can be combined in a mathematical formula, the result 40 of which is the input for the sigmoidal transfer function to form an estimate of the probability of inflammatory status 50. That value 50 can be transformed to a value of relevance 80 to an overall patient response probability 200 via application of a weighing 60.

FIG. 5 illustrates one example of input parameters being combined to formulate a probability associated with a selected biological phenomenon, in this instance, tumour foreignness. Again, the general process is described in relation to FIG. 1a. In this example, tumour foreignness is calculated from optional input parameters, tumour mutation burden (TMB) from tissue or blood sample, neo-antigen burden (NAB) and loss of HLA expression. The latter has a negative contribution, while the former two are alternative positive contributors. In this example, input parameters for the biological phenomenon "tumour foreignness" 500 are shown in FIG. 5 and comprise: TMB 501, NAB 502, and Loss of HLA expression 502. TMB 501 as an input parameter can be generated from various assays, for example, assays relating to Oncomine 510, NeoType 511, Foundation 512. Input parameters 501, 502 and 503 can be an input for various sigmoidal transfer functions which map the input parameter to a contribution to tumour foreignness 500. The transfer function for TMB in this example is Sigm (10 log TMB) 520; the transfer function for NAB is sigm 521; the transfer function in this example for Loss of HLA expression is 1-sigm 522. Those mapped/transformed input parameters can then be combined to form a score for a patient relating to tumour foreignness 500.

In the example of FIG. 5, only tumour mutation burden TMB is available. From the available assays (e.g. Oncomine, NeoType and Foundation Medicine) the results of the Oncomine assay, measuring 409 genes is available. The transfer function used in the example is a sigmoidal with a normalized input range from 0 to 2, an inflection point of 1 and a slope of 2. In this example, the equation is modified such that the output will be 0 and 1 at the respective extremes within an epsilon that can be specified.

Figure 5A:
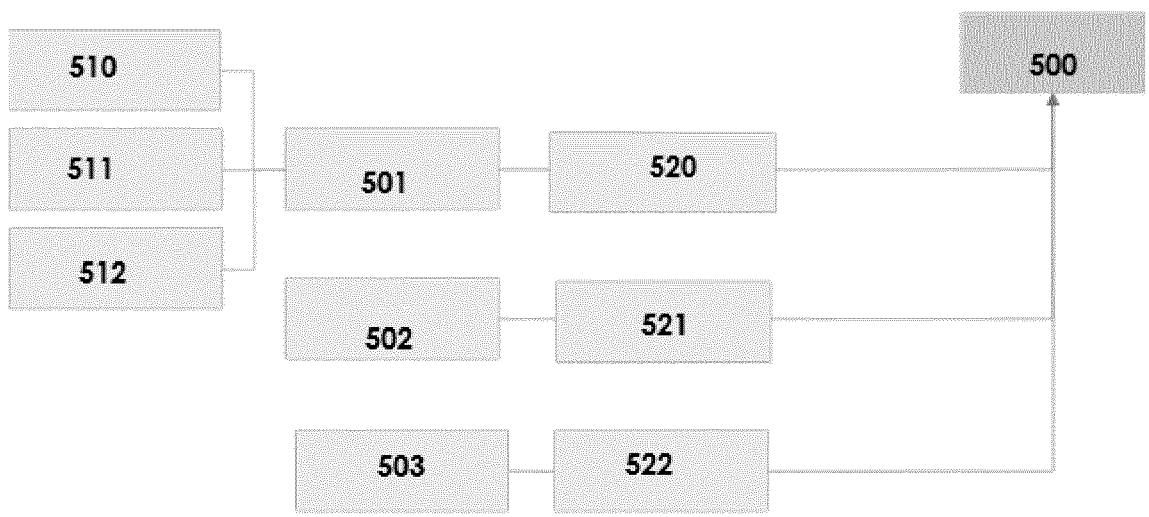
FIG. 5a illustrates a further example of input parameters being combined to formulate a score associated with a selected biological phenomenon.
Figure 5B:
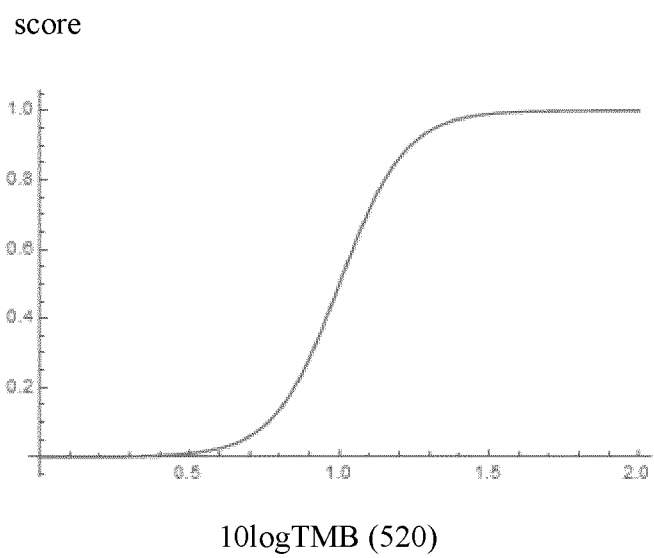

FIG. 5b illustrates a transfer function for use with TMB as an input parameter in the example of FIG. 5a. Having a measured TMB of the patient of 16 mutations/Mbase the transfer function gives a value of 0.867 (using an epsilon of 0.01).

Since there is no input available for NAB and Loss of HLA, in this example, the value of 0.867 is the score for tumour foreignness.

Input parameters can be prioritized, meaning that in the absence of a value of a higher priority input parameter a lower priority input is chosen which has a different transfer function. If all input parameters of relevance to a particular biological phenomenon are lacking, a score associated with that biological parameter may be set to have a neutral contribution to a calculated overall score indicative of a likely patient response to a therapy. That calculated score may, for example, comprise a quantitative value representative of overall response probability 200.

Various input parameters may be of relevance to and therefore used to calculate or determine a score or probability associated with each biological phenomenon of potential relevance to immune response of a patient.

Examples of input parameters of relevance to some possible biological parameters are given in the following table:

| Category/Biological Phenomenon | Marker | Value | Unit |
|---|---|---|---|
| Checkpoint Expression | PD-L1 | 50 | % |
| | CTLA-4 | — | |
| Tumor | TMB | 20 | 1/Mb |
| Foreignness | MSI | — | — |
| | Smoking | 100 | ppy |
| Immune Infiltrate | TIL | 5 | % |
| | CD8 | 3 | % |
| Tumor Metabolism | LDH | 1400 | IU/L |
| | SUV | 16 | — |
| | TLG | — | |
| Exhaustion (T cell dysfunction) | PD-1 | 1 | % |
| | LAG-3 | — | % |
| | TIM-3 | — | % |
| Inflammatory Status | AEC | 789 | 1/μL |
| | NLR | 4.5 | — |
| | ALI | 20 | — |
| | CRP | 8.2 | mg/dL |
| | IL-6 | 23 | pg/mL |
| | IFN-γ | — | pg/mL |
| | BMI | 26 | kg/m2 |

In one embodiment, the quality of an input parameter and/or lack of input can be used to calculate a confidence interval for each biological phenomenon. If creating an overall score in relation to a given patient, all confidence intervals across biological phenomena can be combined and normalized to arrive at a confidence interval for the overall score 200.

As can be seen schematically in FIG. 2, values of the biological phenomena and overall response probability can be presented in a user interface to the clinician optionally with an indication of their importance to the overall response probability 200 allowing a clinician to better understand a patient profile and judge the value of the model calculations.

Model Architecture

A model for assessing likely overall response of a patient may generally be assembled as follows:

A response prediction estimate P uses as input a number of estimates of biological phenomena $f_1, f_2, \ldots, f_n$. According to described arrangements, those phenomena may be selected to reflect how a clinician may reason about a condition and suitability of a cancer patient to an immunotherapy, including properties indicative of a state of a patient's immune system. Each phenomenon $f_i$ is estimated by a probability $p_i$ between zero and one. More detail is provided below regarding how the biological phenomena can be quantified, typically using multiple raw measurements.

A phenomenon $f_i$ is either positive, meaning that a higher $p_i$ will generally result in a higher response probability estimate P, or a phenomenon $f_i$ is negative, meaning that a higher $p_i$ will generally result in a lower response probability estimate P. A response prediction model according to a general arrangement may use a function G having as arguments the estimates of the biological phenomena. Accordingly, a response probability estimate P is given by $$P = G(x(p_1), x(p_2), \ldots, x(p_n))$$

where $x(p_i) = p_i$ when $f_i$ is positive, and $x(p_i) = 1 - p_i$ when $f_i$ is negative.

The function G is based on an approximation of a joint probability distribution of P, $p_1, p_2, \ldots p_n$. Depending on the state of knowledge on the joint probability distribution, G may initially be selected to be relatively simple.

For example, in one arrangement, G can be initially chosen as a weighted sum, given by $$G(x(p_1), x(p_2), \ldots, x(p_n)) = \sum_{i=1}^{n} w_i \cdot x(p_i)$$

where the weights $w_i$ can be chosen such that $w_i \in [0,1]$ and $\sum_{i=1}^{n} w_i = 1$.

The larger a weight $w_i$ the larger its influence on the estimated response probability.

Arrangements recognise that creation of an appropriate and relevant model may be such that the model G is adapted as more knowledge becomes available. That adaptation may occur as a result of new information regarding correlation between individual biomarkers.

Adaptation may, for example, be such that a linear term $x(p_i)$ is replaced by a more appropriate non-linear one (such as $\log(x(p_i))$ or $x(p_i)^{c_i}$ for suitably chosen exponent $c_i$). Furthermore, additional terms may be added, for example, quadratic terms $w_{ij} \cdot x(p_i) \cdot x(p_j)$ or higher-order terms.

It will be appreciated that function G is described here as a possible embodiment and arrangements may encompass more complicated models that nevertheless make explicit use of the biological phenomena as intermediate quantities, for example, in some arrangements, Bayesian networks may be used.

Some arrangements may provide for estimation of various biological phenomena, and models according to some arrangements are configured to generate confidence estimates in relation to each of those phenomena.

In particular, some arrangements may be such that for each phenomenon $f_i$ a confidence interval $[l_i, u_i]$ is estimated, such that $$0 \leq l_i \leq p_i \leq u_i \leq 1.$$

Depending on the measurements/images that have been used to estimate $p_i$, the corresponding confidence interval will be smaller or larger. Confidence intervals associated with an individual $f_i$ can be used to estimate a confidence interval for the response probability estimate P. In other words, using confidence intervals $[l_i, u_i]$, a confidence interval [L, U] may be computed for P.

Arrangements may be configured to provide a decision support system capable of appropriately handling missing data. According to some arrangements, if there is no available data to directly estimate the probability of one or more of the phenomena $f_i$, then a probability $p_i$ and corresponding $[l_i, u_i]$ are estimated on the basis of a probability distribution of $p_i$ for the specific population at hand, whenever available. If that is unavailable, some arrangements are configured such that a probability is, for example, estimated by $p_i = 0.5$ and $[l_i, u_i] = [0,1]$.

Arrangements may operate such that repeated sampling from confidence intervals of the phenomena that are used as arguments of function G, using an appropriate probability distribution, allows for estimation of a confidence interval [L, U]. It will be appreciated that if, for a given phenomenon no probability distribution is available and for that phenomenon $f_i[l_i, u_i] = [0,1]$, it is possible for arrangements to be configured to use a uniform distribution over interval [0,1].

Models according to described arrangements may be configured to compute a response probability estimate P and a confidence interval [L, U]. As a result, clinicians can be supported in making a decision regarding whether or not a patient, or group of patients, is likely to benefit from a given immunotherapy and how certain the computation model was in producing the estimate.

It will be appreciated that some arrangements may also allow for visualisation of the probabilities $p_i$ and corresponding confidence intervals $[l_i, u_i]$ in relation to one or more biological phenomena that are recognized by clinicians. As a result of such an arrangement, clinicians may obtain a better insight into the state of the patient and the ingredients that have been used to come up with the overall response probability estimate P.

ILLUSTRATIVE EXAMPLE

In a scenario where eight biological phenomena have been recognised as being of relevance to likely response of a patient to an immunotherapy, let each biological phenomena be represented by an associated quantified probability: $p_1, p_2, \ldots, p_8$, each in the interval $[0,1]$.

According to a general case, each biological phenomenon may be such that one or more biomarkers can be used to come to the given probability $p_i$. In addition, it will be appreciated that depending on the reliability of the biomarkers used and the sensitivity of the equipment to measure the used biomarkers, the corresponding confidence interval $[l_i, u_i]$ will be smaller or larger.

According to this example, probabilities and corresponding confidence intervals are given by the following table.

| index i | Influence of response probability | probability $p_i$ | lower bound $l_i$ | upper bound $u_i$ |
|---|---|---|---|---|
| 1 | + | 0.80 | 0.77 | 0.83 |
| 2 | + | 0.90 | 0.89 | 0.91 |
| 3 | − | 0.30 | 0.25 | 0.35 |
| 4 | − | 0.40 | 0.38 | 0.42 |
| 5 | + | 0.30 | 0.25 | 0.35 |
| 6 | + | 0.90 | 0 85 | 0.95 |
| 7 | − | 0.50 | 0.49 | 0.51 |
| 8 | + | 0.70 | 0.65 | 0.75 |

Let response probability P be estimated by weighted sum $$P = \sum_{i=1}^{n} w_i \cdot x(p_i)$$

with weights given by the following table. In this example, the sum of the weights equals one.

| index i | weight $w_i$ |
|---|---|
| 1 | 0.20 |
| 2 | 0.20 |
| 3 | 0.20 |
| 4 | 0.15 |
| 5 | 0.10 |
| 6 | 0.05 |
| 7 | 0.05 |
| 8 | 0.05 |

It is then easily seen that the response probability in this example can be estimated by $P=0.20 \cdot 0.80+0.20 \cdot 0.90+0.20 \cdot (1-0.30)+0.15 \cdot (1-0.40)+0.10 \cdot 0.30+0.05 \cdot 0.90+0.05 \cdot (1-0.50)+0.05 \cdot 0.70=0.705.$ For simplicity, in this example, the confidence interval represents an interval from which it is possible to draw samples uniformly at random to estimate the confidence interval $[L, U]$, implicitly assuming that the eight biological phenomena are independent.

In reality, samples should be drawn from their joint probability distribution, but to simplify this example, examples are drawn independently from the different confidence intervals, multiple times, to obtain a distribution for P for which we can estimate a 95% confidence interval around P. Sampling 10,000 times in relation to the above example gives a 95% confidence interval given by [0.66, 0.74].

In one example, suppose that a value for $p_8$ is missing. According to some arrangements, a neutral value of 0.5 may be assumed and it is possible to then sample from interval [0,1] instead of interval [0.65, 0.75] to estimate the confidence interval. Such an approach results in an adapted output of P=0.695 and an adapted confidence interval $[L, U]$ given by [0.64, 0.74]. It can be seen that since the weight of this input is relatively low, the fact that its value is missing does not have a significant impact on the response probability estimate.

In one example, suppose a value for $p_2$ is missing. Adopting the approach given above gives an adapted output of P=0.625 and an adapted 95% confidence interval $[L, U]$ given by [0.50, 0.74]. A more substantial adaptation of the response probability estimate and a correspondingly larger confidence interval can be observed.

Quantifying Biological Phenomena

Some arrangements may provide for computation of quantity $p_i$ for each biological phenomenon $f_i$. These quantities, together with their corresponding confidence intervals, can be visualized for a user.

It will be appreciated that multiple measurements and/or demographic features can be used as an input in a transfer function dedicated to a phenomenon under consideration. According to some arrangements, computation may include two steps: a primary step may include addition or multiplication of measurement data; and a secondary step comprising a sigmoidal normalization function mapping it to an output in the interval [0,1].

Alternative approaches to adding or multiplying multiple measurement input data, may comprise making conditional selections of the available input data. Such conditional selection can form part of a transfer function used to compute quantity $p_i$ for a given phenomenon $f_i$.

It will be appreciated that some phenomena can be quantified in various ways which may differ in, for example, cost and reliability. Arrangements may be configured such that depending on what data is available for a given patient, the input(s) used are those which are most likely to give the most reliable result. This can be reflected in a confidence interval which is smaller than one which would be obtained if less reliable data is used.

Arrangements may therefore be such that a confidence interval $[l_i, u_i]$ associated with a phenomenon $f_i$ is determined by the confidence intervals of the used input measurements and by the reliability of the used data. The confidence intervals of the used input measurements can, for example, be derived from specifications of instruments used to measure an input. Those confidence intervals can be used to estimate the confidence interval $[l_i, u_i]$ in the same way as described above (for transforming the confidence intervals $[l_i, u_i]$ to a confidence interval $[L, U]$). If in the computation of $p_i$ conditional selections are used, then the reliability of the used selection can be used to broaden $[l_i, u_i]$ whenever a less reliable computation is used.

Arrangements described may be used by clinicians in their daily practice in the treatment of individual cancer patients. A visualization tool based upon described arrangements may be used to support meetings of clinical boards and can also be used in the analysis and management of clinical trials for immunotherapy agents.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

Features of some arrangements are set out in the following numbered paragraphs:

1. A method of generating an indication of relevance associated with a selected biological phenomenon indicative of condition of an immune system of a patient, said selected biological phenomenon being associated with response of a patient to a chosen therapy, said method comprising:
    determining one or more measurable input parameters characteristic of said patient and associated with said biological phenomenon;
    mapping said one or more input parameters to a contribution to a score associated with said selected biological phenomenon; and
    combining said mapped contributions across said one or more input parameters to calculate said score associated with said selected biological phenomenon.

2. A method according to paragraph 1, wherein calculating said score associated with said selected biological phenomenon comprises:
    determining an absence of available measurable input parameters of relevance to one or more said selected biological phenomenon and
    setting a neutral contribution to said selected biological phenomenon for which there is an absence of available measurable input parameters; and
    combining said mapped contributions across said one or more input parameters to calculate said score associated with said selected biological phenomenon.

3. A method according to any preceding paragraph, wherein said one or more measurable input parameter of said patient comprises a plurality of interchangeable measurable input parameters, having different reliability rankings, and said method comprises: selecting one or more of said interchangeable measurable input parameters having higher reliability ranking than the remaining measurable input parameters.

4. A method according to any preceding paragraph, wherein determining a confidence interval for said score associated with said biological phenomenon comprises:
    determining a confidence interval and indication of reliability associated with said one or more measurable input parameters mapped to a selected biological phenomenon; and
    generating a confidence interval associated with said biological phenomenon based on said mapped contributions across said one or more input parameters.

5. A method according to any preceding paragraph, wherein said method further comprises: combining said one or more indication of relevance of one or more biological phenomena to response of said patient to generate an indication of overall response of said patient to said chosen therapy.

6. A method according to paragraph 5, wherein said indication of overall response comprises a response probability associated with said patient.

7. A method according to paragraph 5 or paragraph 6, wherein combining said one or more indication of relevance comprises:
    selecting a plurality of biological phenomena of relevance to suitability of a patient for said chosen therapy, said biological phenomena comprising one or more phenomenon indicative of condition of an immune system of said patient;
    determining said calculated score associated with each of said selected biological phenomena;
    assigning a significance to said selected biological phenomena to an overall response of said patient to said chosen therapy; and
    combining the calculated score and assigned significance across said selected plurality of biological phenomena to generate said indication of overall response of said patient to said chosen therapy.

8. A method according to paragraph 7, wherein said method comprises generating a quantitative indication of relevance of each said selected plurality of biological phenomena to said overall response of said patient to chosen therapy.

9. A method according to paragraph 7 or paragraph 8, wherein assigning a significance to said selected biological phenomena comprises weighting said phenomena according to whether they have a positive or negative impact upon response of said patient to said chosen therapy.

10. A method according to any one of paragraphs 7 to 9, wherein combining said one or more indication of relevance of one or more biological phenomena to said overall response of said patient to generate said indication of overall response of said patient to said chosen therapy comprises one or more of: linear combination of said calculated score and assigned significance; quadratic or higher order combination of said calculated scores and assigned significance, a Bayesian network combination of scores and assigned significance.

11. A method according to any one of paragraphs 7 to 10, wherein said method comprises:
    generating a confidence interval for said indication of overall response of said patient to said chosen therapy using a determined confidence interval for each score associated with said selected plurality of biological phenomena and said combination selected for combining said calculated score and assigned significance across said selected plurality of biological phenomena.

12. A method according to any preceding paragraph, wherein said chosen therapy comprises: checkpoint inhibition immunotherapy for treatment of cancer.

13. A method according to any preceding paragraph, wherein said biological phenomena of relevance to suitability of a patient for said chosen therapy comprise: clinically understandable biological phenomena relevant to expected response of said patient to said chosen therapy.

14. A method according to any preceding paragraph, wherein said immunotherapy comprises a cancer treatment immunotherapy and said biological phenomena comprise one or more of: tumour foreignness; tumour metabolism; tumour aggressiveness; inflammatory status; tumour infiltration, T-cell dysfunction; checkpoint expression.

15. Apparatus configured to generate an indication of relevance associated with a selected biological phenomenon indicative of condition of an immune system of a patient, said selected biological phenomena being associated with response of a patient to a chosen therapy, said apparatus comprising:
 memory having computer readable instructions stored therein; and a processor configured to execute said computer readable instructions to:
 determine one or more measurable input parameters characteristic of said patient and associated with said biological phenomenon;
 map said one or more input parameters to a contribution to a score associated with said selected biological phenomenon; and
 combine said mapped contributions across said one or more input parameters to calculate said score associated with said selected biological phenomenon.

The invention claimed is:

1. A method of administering a cancer therapy to a cancer patient, comprising assessing relevance of a selected biological phenomenon to response of a patient to a chosen therapy, said biological phenomenon being indicative of condition of an immune system of the cancer patient, comprising:
 determining one or more measurable input parameters from one or more diagnostic modalities comprising: radiology, pathology and clinical chemistry, wherein the input parameters include at least one of a plurality of biomarkers and further wherein said input parameters are: (i) characteristic of said patient and (ii) associated with said biological phenomenon and (iii) configured to generate at least one of score and/or visualization;
 mapping said one or more input parameters to a contribution to a score associated with said selected biological phenomenon;
 combining said mapped contributions across said one or more input parameters to calculate said score associated with said selected biological phenomenon, said score comprising a quantitative indication derived from the said score and the input parameters, wherein the quantitative indication is indicative of said relevance of said selected biological phenomenon to response of a patient to a chosen therapy, wherein the said score is calculated based on the following steps: (i) determining an absence of available measurable input parameters of relevance to one or more said selected biological phenomenon, (ii) setting a neutral contribution to said selected biological phenomenon for which there is an absence of available measurable input parameters, and (iii) combining said mapped contributions across one or more input parameters;
 determining a confidence interval for said score associated with said biological phenomenon by: (i) determining a confidence interval and indication of reliability associated with said one or more measurable input parameters mapped to said selected biological phenomenon; and (ii) generating a confidence interval associated with said biological phenomenon based on said mapped contributions across said one or more input parameters;
 determining, based on the calculated score and confidence interval, that the cancer patient will respond positively to the chosen therapy; and
 administering, after receiving said calculated score and confidence interval and determining that the cancer patient will respond positively to the chosen therapy, the chosen cancer therapy.

2. The method of claim 1, wherein said one or more measurable input parameter of said patient comprises a plurality of interchangeable measurable input parameters, having different reliability rankings, and said method comprises:
 selecting one or more of said interchangeable measurable input parameters having higher reliability ranking than the remaining measurable input parameters.

3. The method of claim 1, wherein said method further comprises:
 combining said one or more indication of relevance of one or more biological phenomena to response of said patient to generate an indication of overall response of said patient to said chosen therapy.

4. The method of claim 3, wherein said indication of overall response comprises a response probability associated with said patient.

5. The method of claim 3, wherein combining said one or more indication of relevance comprises:
 selecting a plurality of biological phenomena of relevance to suitability of a patient for said chosen therapy, said biological phenomena comprising one or more phenomenon indicative of condition of an immune system of said patient;
 determining said calculated score associated with each of said selected biological phenomena;
 assigning a significance to said selected biological phenomena to an overall response of said patient to said chosen therapy; and
 combining the calculated score and assigned significance across said selected plurality of biological phenomena to generate said indication of overall response of said patient to said chosen therapy.

6. The method of claim 5, wherein said method comprises:
 generating from: (i) said score associated with each of said selected biological phenomena; (ii) said assigned significance to an overall response of said patient to said chosen therapy; and (iii) said indication of overall response of said patient to said chosen therapy; a quantitative indication of relevance of each said selected plurality of biological phenomena to said overall response of said patient to chosen therapy.

7. The method of claim 5, wherein assigning a significance to said selected biological phenomena comprises weighting said phenomena according to whether they have a positive or negative impact upon response of said patient to said chosen therapy.

8. The method of claim 5, wherein combining said one or more indication of relevance of one or more biological phenomena to said overall response of said patient to generate said indication of overall response of said patient to said chosen therapy comprises one or more of:
- a linear combination of said calculated score and assigned significance;
- a quadratic or higher order combination of said calculated scores and assigned significance; and
- a Bayesian network combination of scores and assigned significance.

9. The method of claim 5, wherein said method comprises:
generating a confidence interval for said indication of overall response of said patient to said chosen therapy using a determined confidence interval for each score associated with said selected plurality of biological phenomena and said combination selected for combining said calculated score and assigned significance across said selected plurality of biological phenomena.

10. The method of claim 1, wherein said chosen therapy comprises: checkpoint inhibition immunotherapy for treatment of cancer.

11. The method of claim 1, wherein said biological phenomena of relevance to suitability of a patient for said chosen therapy comprise: clinically understandable biological phenomena relevant to expected response of said patient to said chosen therapy.

12. The method of claim 1, wherein said chosen therapy comprises a cancer treatment immunotherapy and said biological phenomena comprise one or more of: tumour foreignness; tumour metabolism; tumour aggressiveness; inflammatory status; tumour infiltration, T-cell dysfunction; and checkpoint expression.

13. A system for administration of a cancer therapy to a cancer patient, the system configured to assess relevance of a selected biological phenomenon to response of a patient to a chosen therapy, said biological phenomenon being indicative of condition of an immune system of a patient, said system comprising:
- memory having computer readable instructions stored therein;
- a processor configured to execute said computer readable instructions to: (1) determine one or more measurable input parameters from one or more diagnostic modalities comprising radiology, pathology and clinical chemistry, wherein the input parameters include at least one of plurality of biomarkers and further wherein said input parameters are: (i) characteristic of said patient and (ii) associated with said biological phenomenon and (iii) configured to generate at least one or score and/or visualization; (2) map said one or more input parameters to a contribution to a score associated with said selected biological phenomenon; and (3) combine said mapped contributions across said one or more input parameters to calculate said score associated with said selected biological phenomenon, said score comprising a quantitative indication derived from the said score and the input parameters, wherein the quantitative indication is indicative of said relevance of said selected biological phenomenon to response of a patient to a chosen therapy wherein the said score is calculated based on the following steps: (i) determining an absence of available measurable input parameters of relevance to one or more said selected biological phenomenon, (ii) setting a neutral contribution to said selected biological phenomenon for which there is an absence of available measurable input parameters, and (iii) combining said mapped contributions across one or more input parameters; (4) determine a confidence interval for said score associated with said biological phenomenon by: (i) determining a confidence interval and indication of reliability associated with said one or more measurable input parameters mapped to said selected biological phenomenon; and (ii) generating a confidence interval associated with said biological phenomenon based on said mapped contributions across said one or more input parameters; and (5) determine, based on the calculated score and confidence interval, that the cancer patient will respond positively to the chosen therapy;
- a chosen therapy administered to the cancer patient after determining that the cancer patient will respond positively to the chosen therapy.

14. A method for administering a cancer therapy to a cancer patient, the method comprising:
receiving: (i) a calculated score comprising a quantitative indication indicative of a relevance of the cancer patient's immune system to a response of the cancer patient to a chosen cancer therapy; and (iii) a confidence interval associated with said calculated score, wherein the calculated score and the confidence interval are calculated by:
- determining one or more measurable input parameters from one or more diagnostic modalities comprising: radiology, pathology, and clinical chemistry, wherein said measurable input parameters include at least one of a plurality of biomarkers and further wherein said input parameters are: (i) characteristic of said patient; and (ii) associated with said cancer patient's immune system; and (iii) configured to generate at least said calculated score;
- mapping said one or more input parameters to a contribution to a score associated with said cancer patient's immune system; and
- combining said mapped contributions across said one or more input parameters to calculate said score associated with said cancer patient's immune system, said score comprising a quantitative indication derived from the said score and the input parameters, wherein the quantitative indication is indicative of said relevance of said cancer patient's immune system to response of the cancer patient to a chosen therapy, wherein the said score is calculated based on the following steps: (i) determining an absence of available measurable input parameters of relevance to said cancer patient's immune system, (ii) setting a neutral contribution to said cancer patient's immune system for which there is an absence of available measurable input parameters, and (iii) combining said mapped contributions across one or more input parameters; and
- determining a confidence interval for said score associated with said cancer patient's immune system by: (i) determining a confidence interval and indication of reliability associated with said one or more measurable input parameters mapped to said cancer patient's immune system; and (ii) generating a confidence interval associated with said cancer patient's immune system based on said mapped contributions across said one or more input parameters; and
determining, based on the received calculated score and confidence interval, that the cancer patient will respond positively to the chosen therapy; and administering, after receiving said calculated score and confidence interval and determining that the cancer patient will respond positively to the chosen therapy, the chosen cancer therapy.

15. The method of claim 14, wherein the chosen cancer therapy is one or more of immunotherapy, radiotherapy, and chemotherapy.

16. The method of claim 1, wherein the chosen cancer therapy is one or more of immunotherapy, radiotherapy, and chemotherapy.

17. The system of claim 13, wherein the chosen cancer therapy is one or more of immunotherapy, radiotherapy, and chemotherapy.

18. The system of claim 13, wherein said one or more measurable input parameters comprise a plurality of interchangeable measurable input parameters, each having different reliability rankings, and determining the one or more measurable input parameters from the one or more diagnostic modalities comprises selecting one or more of said interchangeable measurable input parameters having a higher reliability ranking than remaining measurable input parameters.

19. The method of claim 14, wherein said one or more measurable input parameters comprise a plurality of interchangeable measurable input parameters, each having different reliability rankings, and determining the one or more measurable input parameters from the one or more diagnostic modalities comprises selecting one or more of said interchangeable measurable input parameters having a higher reliability ranking than remaining measurable input parameters.

20. The method of claim 14, further comprising combining said one or more indication of relevance of one or more biological phenomena to response of said patient to generate an indication of overall response of said patient to said chosen therapy.

* * * * *